United States Patent
Petkov et al.

(10) Patent No.: US 12,354,216 B2
(45) Date of Patent: Jul. 8, 2025

(54) SYSTEMS AND METHODS FOR AUTOMATED RENDERING

(71) Applicant: Siemens Healthineers AG, Forchheim (DE)

(72) Inventors: Kaloian Petkov, Lawrenceville, NJ (US); Sandra Sudarsky, Bedminster, NJ (US); Rishabh Shah, Wentworth Point (AU); Christoph Vetter, Hopewell, NJ (US)

(73) Assignee: Siemens Healthineers AG, Forchheim (DE)

( * ) Notice: Subject to any disclaimer, the term of this patent is extended or adjusted under 35 U.S.C. 154(b) by 340 days.

(21) Appl. No.: 17/931,257

(22) Filed: Sep. 12, 2022

(65) Prior Publication Data

US 2024/0087218 A1 Mar. 14, 2024

(51) Int. Cl.
*G06T 15/50* (2011.01)
*G16H 30/40* (2018.01)

(52) U.S. Cl.
CPC ............ *G06T 15/506* (2013.01); *G16H 30/40* (2018.01); *G06T 2200/24* (2013.01); *G06T 2207/20021* (2013.01); *G06T 2210/41* (2013.01)

(58) Field of Classification Search
CPC ............... G06T 15/506; G06T 2200/24; G06T 2207/20021; G06T 2210/41; G06T 15/08; G06T 2219/2024; G06T 19/20; G06T 15/04; G16H 30/40; G16H 40/60; G16H 50/20; G16H 50/50; G16H 30/20

See application file for complete search history.

(56) References Cited

U.S. PATENT DOCUMENTS

| | | |
|---|---|---|
| 10,354,451 B2 | 7/2019 | Petkov et al. |
| 2013/0346891 A1 | 12/2013 | Hayball |
| 2017/0061687 A1 | 3/2017 | Hong et al. |
| 2018/0271460 A1 | 9/2018 | Geiger et al. |
| 2018/0350130 A1 | 12/2018 | Westerhoff et al. |
| 2021/0279952 A1* | 9/2021 | Chen ................. G06T 17/00 |

OTHER PUBLICATIONS

Extended European Search Report (EESR) mailed Jul. 10, 2024 in corresponding European Patent Application No. 23196158.2.

* cited by examiner

*Primary Examiner* — Qian Yang

(57) ABSTRACT

Systems and methods for determining rendering parameters based on authored snapshots or templates. In one aspect, clinically relevant snapshots of patient medical data are created by experts to support educational or clinical workflows. Alternatively, the snapshots are created by automation processes from AI-based organ and disease segmentations. In another aspect, clinically relevant templates are generated. Rendering parameters are derived from the snapshots or templates, stored, and then applied for either rendering new data or interactive viewing of existing data.

5 Claims, 12 Drawing Sheets
(8 of 12 Drawing Sheet(s) Filed in Color)

SYSTEMS AND METHODS FOR AUTOMATED RENDERING

FIELD

This disclosure relates to image rendering, such as rendering for medical imaging applications.

BACKGROUND

Image processing and imaging visualization have provided a significant impact on a wide spectrum of media such as animations, movies, advertising, and video games. One area that has benefited greatly from imaging processing and visualization is medical imaging. For medical imaging, volume rendering of medical images has become a standard for many procedures, educational studies, and diagnostics. The visualization of human organs and body regions using volume rendering color capabilities may be used in several medical imaging modalities such as Computed Tomography (CT) and Magnetic Resonance Imaging (MRI).

Traditional volume visualization methods may be based on rendering techniques such as ray casting methods. Ray casting simulates only the emission and absorption of radiant energy along the primary viewing rays through the volume data. The emitted radiant energy at each point is absorbed according to the Beer-Lambert law along the ray to the observer location with absorption coefficients derived from the patient data. Renderers typically compute shading using only the standard local shading models at each point along the ray (e.g., the Blinn-Phong model), based on the local volume gradients (local illumination). While fast, these methods do not simulate the complex light scattering and extinction associated with photorealism (global illumination).

Newer, advances in rendering have been able to provide a physical rendering algorithm that simulates the complex interaction between photons and the scanned anatomical image to obtain photo-realistic images and videos. As an example, a process referred to as Cinematic Rendering facilitates a photo-realistic image with seemingly real-life ambient and light effects which suggest to the human eye that this is "real". Additional features may include high-performance rendering and highly advanced camera techniques, such as variable aperture diameters and motion blurring. Three-dimensional volume rendering capabilities may be used for visualization of the complex internal anatomy of a patient. Furthermore, volume rendering techniques offer relevant information for pre-operative planning as well as post-operative follow-up.

In terms of high-performance rendering from the volume of a large amount of data, interactive or real-time rendering may be difficult. Pre-rendering is used, allowing for high-quality rendering to be viewed. While traditional pre-rendered movies offer a high-quality playback, pre-rendered movies only allow for a fixed playback sequence. High quality interactive viewing of large data or a complex scene is often prohibitive due to the intense computer computational power required.

Further, it remains a difficult problem to find the right set of parameters to render medical images showing important structure details for particular disease or showing only relevant information for a specific clinical workflow. Currently, these parameters are selected via presets and heuristics based on the type of scan and the medical image modality and then adjusting them manually until the right image is generated.

SUMMARY

By way of introduction, the preferred embodiments described below include methods, systems, instructions, and computer readable media for determining rendering parameters based on authored snapshots or templates.

In a first aspect, a system including an input interface, an image processing system, and a view platform. The input interface is configured to acquire first image data representing a region of a first patient. The image processing system is configured to input the image data and determine a plurality of optimized rendering settings, the image processing system configured to render the first image data using the plurality of rendering settings or render second image data for the region of a second patient using the plurality of rendering settings and the second image data for the second patient. The viewing platform is configured to provide the rendered first or second image data.

In an embodiment, the input interface comprises an authoring application that is configured to generate one or more clinical snapshots using a physically based Monte Carlo light transport, wherein the image processing system is configured to render the region of the first patient for an interactive viewer using the plurality of rendering settings, and wherein the image processing system is configured to render the region of the first patient using global illumination. The image processing system may be configured to render the region of the second patient and wherein the input interface comprises a medical imaging system configured to acquire image data of the second patient. The image processing system may be configured to render the region of the second patient and wherein the image data comprises a traditional anatomical illustration or a photograph. In an embodiment, the plurality of optimized rendering settings comprises style parameters for the image data.

The first image data may comprise a template for the region, wherein the image processing system is configured to render the region of the second patient, and wherein the image processing system is further configured to segment the second image data and select the first image data from a template database using a full body atlas configured to store one or more templates. The template database may store a plurality of templates including the template, wherein each template in the template database comprises a reference image, viewing parameters, and one or more masks.

In a second aspect, a method for automated rendering from templates, the method comprising acquiring image data; segmenting the image data into one or more segmentation masks; retrieving one or more templates corresponding to the one or more segmentation masks, the one or more templates comprising at least a reference image and viewing parameters; computing, using a differentiable renderer, one or more rendering parameters based on a style of the reference image; and generating an image for the image data using the one or more rendering parameters.

In an embodiment, retrieving the one or more templates comprises registering the one or more segmentation masks against a body atlas configured to store a plurality of different masks of different regions and organs. The image data may be acquired using a medical image device. The one or more templates may be generated from a traditional anatomical illustration or a photograph. The one or more rendering parameters may define a color and a texture of the generated image. The one or more templates may comprise at least reference images for different organs.

In a third aspect, a method for interactive viewing in medical imaging, the method comprising: generating one or more clinical snapshots for a medical imaging scenario using a first rendering algorithm, the clinical snapshot specifying one or more visualization settings for the medical imaging scenario; determining rendering parameters for a second rendering algorithm that approximate the one or more visualization settings from the one or more clinical snapshots; accessing the one or more clinical snapshots using a viewing platform that uses the second rendering algorithm; and rendering using the second rendering algorithm the one or more clinical snapshots.

In an embodiment, the method further includes generating precomputed assets for the one or more clinical snapshots, wherein the interactive viewing using the precomputed assets. Generating the rendering parameters may comprise generating the rendering parameters using differentiable rendering.

The second rendering algorithm may comprise an interactive approximate global illumination method.

In an embodiment, generating comprises generating using automation processes from AI-based organ and disease segmentations.

The viewing platform may comprise an AR or VR system.

The one or more visualization settings may comprise one or more of the following: camera settings, lighting settings, or material settings.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
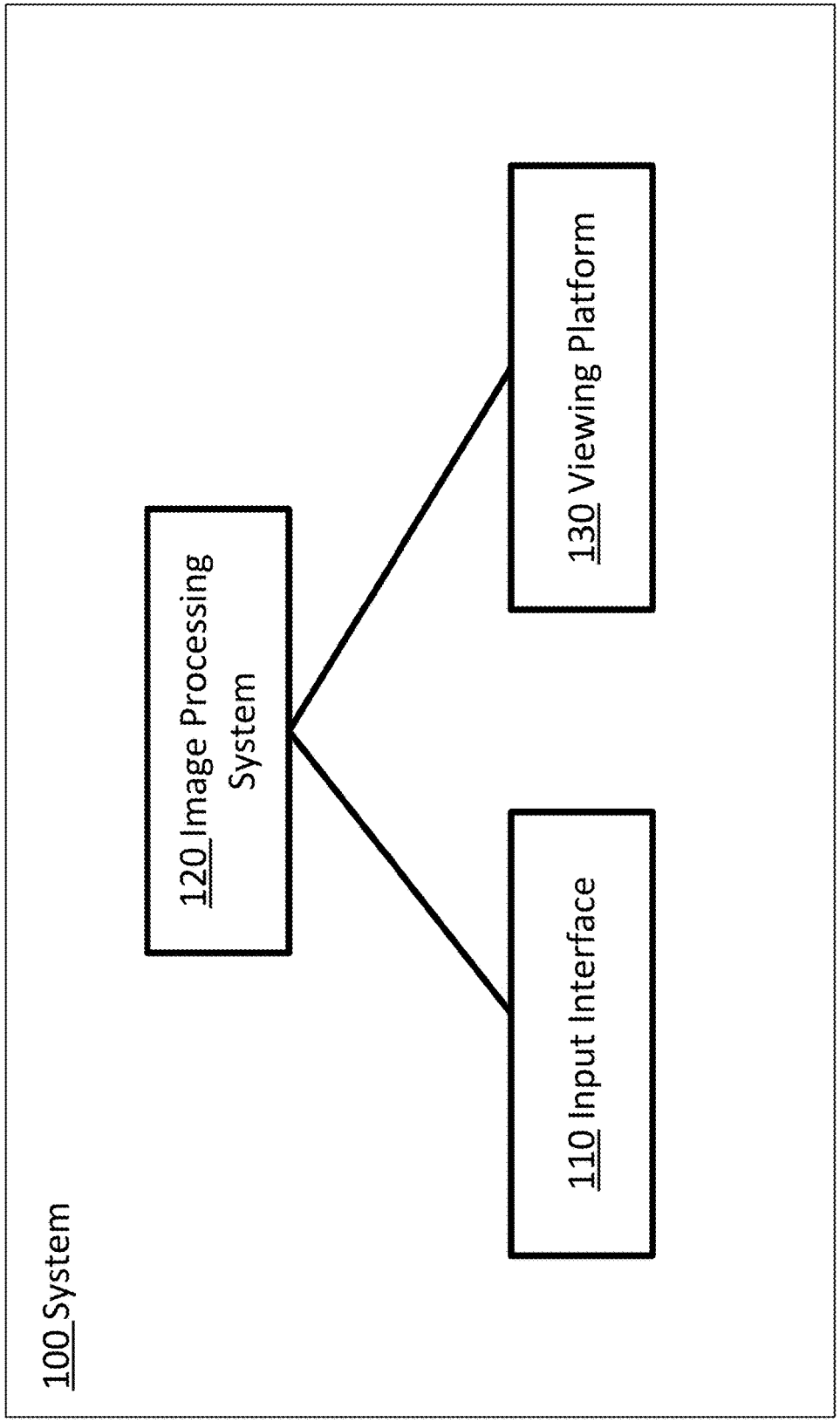
FIG. 1 depicts an embodiment of a system for automated rendering according to an embodiment.

Embodiments described herein provide systems and methods for determining rendering parameters based on authored snapshots or templates. In one aspect, clinically relevant snapshots of patient medical data are created by experts to support educational or clinical workflows. Alternatively, the snapshots are created by automation processes from AI-based organ and disease segmentations. In another aspect, clinically relevant templates are generated. Rendering parameters are derived from the snapshots or templates, stored, and then applied for either rendering new data or interactive viewing of existing data.

Medical volume rendering is a technique often used to visualize computed tomography (CT), magnetic resonance (MR), and ultrasound medical data. Several volume rendering algorithms may be used including an advanced method based on Monte-Carlo path tracing. One such method referred to as Cinematic Rendering (CR) can generate photorealistic depictions of the medical data. These high-quality images can be very advantageous for diagnostics, surgical planning, doctor/patient communication, research and medical training and education. With the right set of parameters, cinematic rendered images can show soft-tissue details, ambient occlusions, and realistic shadows which provide important perceptual information about the depth, shape, and surface characteristics of the underlying data.

In cinematic rendering, the medical data is illuminated using image-based lighting by high dynamic range light probes that can be acquired photographically with 360-degree cameras in order to resemble the lighting condition of a training theater. Such lighting leads to a more natural appearance of the data when compared to images created using only the synthetic light sources that are typically applied in direct volume rendering methods. When also combined with the accurate simulation of photon scattering and absorption, the renderer produces photorealistic images that contain many shading effects observed in nature, such as soft shadows, ambient occlusions, volumetric scattering, and subsurface photon interactions. The result is a hyper-realistic augmented experience that appears natural and intuitive without the technology being a distraction to achieving efficient learning.

Identifying parameters for high quality and realistic rendering may be a challenge. In addition, certain hardware and devices that provide real time use (for example, augmented reality (AR) or virtual reality (VR) application) may not have the computational power or resources to use these advanced rendering techniques. Embodiments provide systems and methods that determine these parameters for both advanced techniques and other rendering algorithms by using an authoring platform and pre-identified styles and visualization parameters.

In general, volume rendering may be represented by a function $f(V, X) \rightarrow I$ that takes a volume $V$ and a set of rendering parameters $X$ and generates a rendered image $I$. For three-dimensional graphics, there are many parameters that can be defined or determined for each scenario. In an example, parameters may include windowing, scaling, level compression, data normalization, or others. As another example, one or more transfer function parameters may be used. Transfer function parameters include classification look-up tables, multi-dimensional transfer functions, tissue-specific transfer functions, or other transfer functions. In another example, one or more lighting design parameters may also be specified. Lighting design parameters include type of virtual lights, position of the virtual light sources, orientation of the virtual light sources, image-based lighting sources, or others. In yet another example, one or more viewing design parameters may be used. Viewing design parameters include type of camera, position of the camera, orientation of the camera, intrinsic parameters for viewing, or others. In other examples, one or more use-case specific parameters may be specified. Use-case specific parameters are settings specific to a given use, such as a particular camera position for a given type of medical report or use of two cameras for stereoscopic viewing.

FIG. 1 depicts an example of a system 100 for automated rendering of medical imaging data. The system 100 includes an input interface 110 configured to acquire image data representing a region of a patient. The image data may be provided as an authored snapshot or a template for a particular region or object. The system further includes an image processing system 120 configured to input the image data and determine a plurality of optimized rendering settings. The optimized settings may represent a visualization style of the image data. When implemented, the optimized settings may be used by an image processor configured to render the image data for an interactive viewer or render new image data for the region. In an example, these settings may contain volume classification presets, different presets highlight different organs and tissues, camera specifications, camera parameters like position, orientation, field of view, fisheye vs. perspective, etc. In an embodiment, the camera may be animated to create more a dynamic visualization. Some of the rendering techniques described in this disclosure enabled real time rendering of these animations at interactive speeds. The settings may further include lighting specifications. Just like camera, lighting settings may also be customized. The type of light source, intensity, animations, etc. can be supported. Material settings may also be used that affect the shading of different materials during rendering.

The input interface 110 is configured to acquire image data representing a region or object of a patient. The image data may be acquired at any point and may be stored in a memory or database for later use. In an example, the image data is data acquired using a medical imaging device. The image data may also be synthetic or generated by an operator. The input interface 110 may include an authoring platform. The authoring platform is used to create clinical snapshots based on different specialized use cases. In one embodiment, the authoring tool allows the expert to specify various visualization settings for the scenario. Clinically relevant snapshots of the patient medical data may be created by experts to support educational or clinical workflows or may be created by automation processes from AI-based organ and disease segmentations. The snapshots store rendering parameter sets for viewing, clipping, classification, animations and rendering styles. There may be different sets for different rendering algorithms. Each set of rendering parameters attempts to reproduce the visualization or style that is generated by the authoring platform. In an example, a view may be generated by an expert or automated system that depicts a certain organ using advanced rendering techniques that provide realistic lighting, textures, etc. An image processing system (parameter engine) generates a set of rendering parameters that attempt to mimic or reproduce the realistic lighting, textures, etc. of the clinical snapshot when rendered using alternative rendering algorithms. In addition, certain assets may be precomputed by a rendering engine for each snapshot for the viewing platform. These assets may include or be rendered with fully rendered proxies, shaded point-clouds, and layered semi-transparent surfaces among others. In an example, the surface color may be derived from the voxel classification color; in addition, ambient occlusions or diffuse global illumination may be baked into the surface color. Lightfields may also be pre-computed from the full quality rendering algorithm.

In an embodiment, pre-rendered videos with the full quality rendering algorithm, e.g., turntable videos for each snapshot may be generated and stored for use with a viewing interface. In an embodiment, pre-computed transitions may be generated for sequences between the precomputed assets. The transitions may include intermediate point cloud and mesh proxies, 3D+time light fields, intermediate AO and irradiance/radiance caches, transition videos using the snapshots as keyframes. Pre-computed volume data may also be used to speed up interactive rendering (in place of on-the-fly lighting computations) Ambient occlusion, irradiance cache, radiance cache, and IVL.

In an embodiment, the clinical snapshots are generated automatically based on clinical requirements and machine analysis of the medical data. Such a system may employ AI-based automated organ segmentation and derive the viewing, clipping and classification rendering parameters based on the resulting organ masks for a given clinical context. In the example of liver ablation planning, liver, vessel, and lesion segmentations from multi-phase CT data may be used as part of the transfer function to provide optimized visual contrast of the vessels against the liver tissue in volume rendering, while principal component analysis of the vessel tree vertices may produce the initial camera parameters. In further embodiments, the rendering parameters may be derived by a differentiable rendering system from image examples.

The input interface 110 may include a platform for generating templates for certain regions or objects. The authoring platform, described above, may be used to generate templates. Alternatively, the templates may be generated from any image data such as photographs or previously generated image data. Templates are organized by the content, region, diagnosis, and/or view that the templates represent. For example, a template may be generated and stored for a particular organ with a particular affliction from a particular view. This template may be used when new data is acquired to transfer the visual settings of the template to the new data in order to provide visualization of the new data that includes rendering settings that have previously been determined to either be beneficial or helpful for analysis or diagnosis.

To generate a template, the content, region, diagnosis, and/or view are first determined. One method uses segmentation to identify and determine these features. A reference image is acquired. The reference image may be a traditional anatomical illustration, a photograph of a surgical procedure, an MPR image, a previously rendered image, etc. The reference image may be identified as a "good" or useful image based on its visualization or depiction of the content therein. In an example of a "good" or useful image, an operator may author a view using the authoring platform. This view may provide optimized visualization settings, for example by accurately and concisely conveying a particular feature of interest. From the reference image (Iref), the system computes a 2D segmentation to generate a collection of anatomical landmarks and binary masks representing objects or features, for example the body organs found in the reference image (Iref). Next, a 2D/3D or 3D/3D registration is applied to the masks against a full body 3D anatomical atlas. The full body 3D anatomical atlas contains masks, landmarks, diagnosis, or other information that may be matched against the reference image (and new data). The registration image-to-atlas may also be provided via a deep learning method by classifying the features or content of the reference image. The template is stored in a database including the tuples (Iref, M, Xv) consisting of the reference image, the generated masks, and the calculated viewing parameters. The viewing parameters may be stored relative to the atlas so the viewing parameters can be easily transferred to other datasets.

Referring back to FIG. 1, the system includes at least one image processing system 120 that is configured to input the image data and determine a plurality of optimized rendering settings. The image processing system 120 may be part of the authoring platform as discussed above or part of an image viewing system (for example, a VR or AR headset or other associated hardware). At least one renderer is provided by the image processing system 120 on site or through the cloud. The at least one renderer may be provided by instructions and the image processor as described below in FIG. 12. During authoring of a clinical snapshot, user-defined rendering parameters may be provided using tools/presets in the authoring application. This process may be automated, for example, using AI based, heuristics, etc. The at least one renderer may also be used in real time when rendering and providing interactive or new data.

Rendering refers to the process of forming a realistic or stylized image from a description of the 3D virtual object (e.g., shape, pose, material, texture), and the illumination condition of the surrounding scene (e.g., light position, distribution, intensity). A rendering engine (or renderer) may input rendering parameters and the volume data to generate an image. Existing physically based rendering algorithms generate images by simulating the propagation of light through detailed virtual scene descriptions. This process can also be interpreted as evaluating a function $f: X \rightarrow Y$, whose high-dimensional input encodes the shape and materials of objects, and whose output $y=f(x)$ is a rendered image that reveals the complex radiative coupling between objects (shadows, interreflection, caustics, etc.). These effects are crucial in the pursuit of photorealism, but the effects may also obscure the individual properties of objects. An inverse process may also be used to identify or estimate the rendering parameters. In an example, the rendering parameters consists of viewing parameters Xv, lighting parameters Xl, material properties Xm, and transfer functions Xt. Certain embodiments use a differentiable rendering engine that poses the problem of finding these parameters as an optimization problem as long as the image-space gradients with respect to these parameters are possible to compute. The objective function may be as simple as minimizing the squared difference between the output image I and a reference image Iref le. The viewing parameters (Xv) that would generate renderings that best approximate the reference image are computed from the registration matrix. The system minimizes the difference between the synthesized and observed data.

In an embodiment, the rendering parameters are adapted/optimized for the target rendering proxy (e.g., point cloud, surfaces, light field). In another embodiment, the rendering parameters may be changed at run time based on user interaction (e.g., viewing, lighting). This may trigger an optimization phase based on the rendering proxy being used or may trigger template evaluations. The system may optimize shading, transparency and point placement when generating the point-cloud proxies. E.g., increase point cloud density in areas of the volume data with high frequency lighting or many overlapping surfaces (applicable to ray selection for light field generation too). The optimization process may employ differentiable rendering. The optimization process may account for expected parameter replacements by the viewing platform—e.g., optimize lighting parameters for the viewing parameters expected for head-tracked VR and AR displays.

The image processing system 120 is further configured to render the region of the first patient for an interactive viewer using the plurality of rendering settings or render the region of a second patient using the plurality of rendering settings. In an embodiment, the clinical snapshot is rendered with a different algorithm than was used to generate the clinical snapshot. Using the pre-computed rendering parameters, assets, transitions, etc. the different algorithm is able to generate a view including the style/visualization of the authored clinical snapshot. In an embodiment, new data is acquired. The new data is matched to identify one or more templates with desirable visual settings. A differentiable renderer is used to transfer the visualization settings or style of the reference image from the template to the new data.

The system 100 further includes a viewing platform 130 that is configured to display or otherwise provide the rendered image to a user. The viewing platform 130 may be an AR or VR system or may be a standard display. The viewing platform may also include other types of displays such as auto-stereo display, light field displays (LFD), projected displays, etc. LFDs are based on a dense "field" of light rays produced by either a high-resolution LCD panel (with optics) or a projector array system. The result is a naturally viewable full-color real-time video 3D display that does not require any glasses. The display can have several people located within its field of view, with each person seeing a slightly different viewpoint, depending on their position, just like a real 3D object. Projection mapping or projected augmented reality may be used, if for example, a camera/projector is used instead of a head mounted display. For projection AR, the projector projects a beam of light onto the work surface or, for example, directly on the parts on which the user is interacting with. 3D displays or stereo displays present normal two-dimensional (2D) images offset laterally by a small amount and displayed separately to the left and right eye. Both of these 2D offset images are then combined in the brain and create the perception of depth. Implementation of the system for both clinical snapshots and using templates is further described below.

Figure 2:
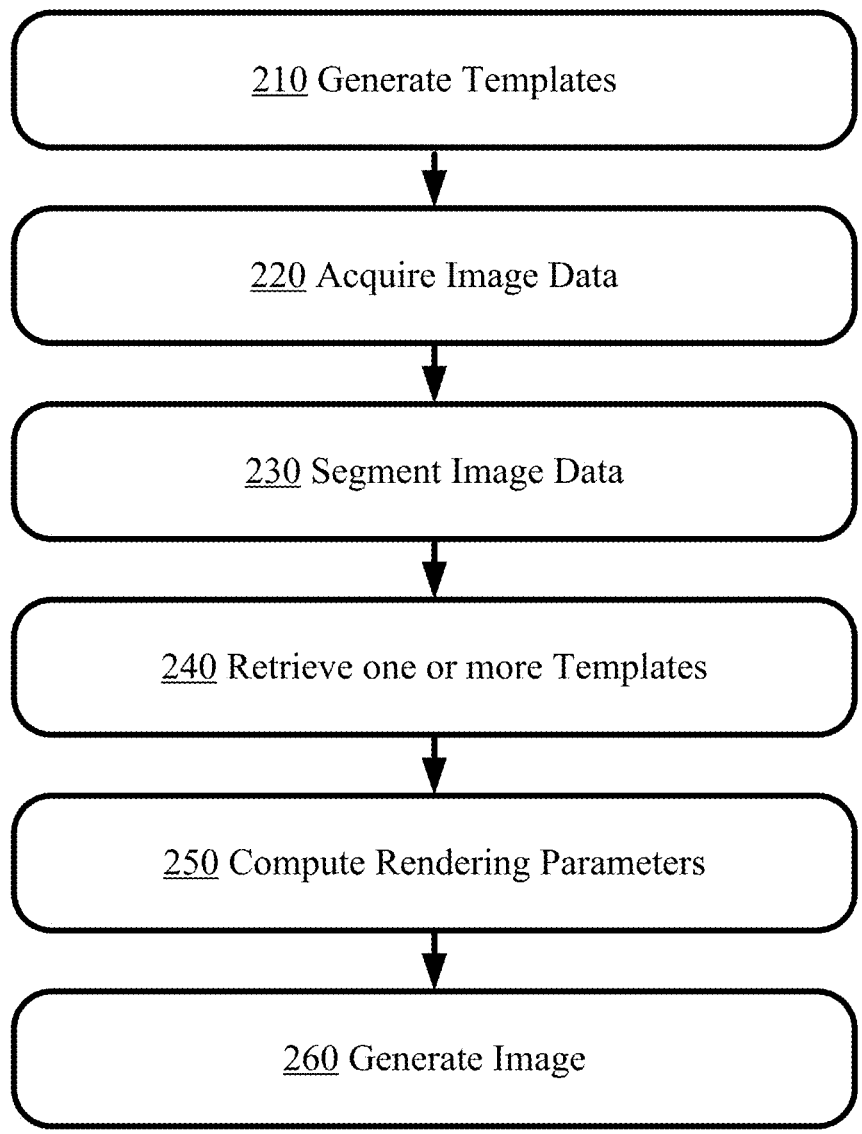
FIG. 2 depicts an example method for using templates to render medical imaging data according to an embodiment.

FIG. 2 depicts an example method for generating clinically relevant templates and applying the templates to new data sets. The acts are performed by the system of FIG. 1, FIG. 3, FIG. 4, FIG. 12, other systems, a workstation, a computer, and/or a server. The acts are performed in the order shown (e.g., top to bottom) or other orders.

As described above, several volume rendering algorithms are available, including a method based on Monte-Carlo path tracing, referred to as cinematic rendering that can generate photorealistic depictions of the medical data. These high-quality images can be very advantageous for diagnostics, surgical planning, doctor/patient communication, research and medical training and education. With the right set of parameters, cinematic rendered images can show soft-tissue details, ambient occlusions and realistic shadows which provide important perceptual information about the depth, shape, and surface characteristics of the underlying data.

Volume rendering can be represented by a function $f(V, X) \rightarrow I$ that takes a volume V and a set of rendering parameters X and generates a 2D rendered image I. The rendering parameters consists of viewing parameters Xv, lighting parameters Xl, material properties Xm, and transfer functions Xt. The inverse problem of finding the parameters X from an Image I is not always possible. Differentiable rendering is a technique which poses the problem of finding these parameters as an optimization problem as long as the image-space gradients with respect to these parameters are possible to compute. The objective function may include minimizing the squared difference between the output image I and a reference image Iref.

Automated rendering using templates may be divided into two steps. During the first (offline) step a database of useful templates is constructed. Each template includes a reference image Iref, a set of segmentation masks describing the content/organs/lesions/landmarks present and the parameters Xv computed via a pose estimation algorithm. During the second (online) step templates (Iref, M, Xv) corresponding to the masks found in the new scan are retrieved and the system computes the remaining set of parameters Xm, Xt, Xl used to transfer the "style" of the reference image to the final image. These parameters are referred to as the "style parameters" as the parameters define the color and texture of the final image.

Generating the templates, e.g., building the template database, may be performed offline or at any point prior to applying the templates. Applying the templates may be performed after acquiring new image data.

Figure 3:
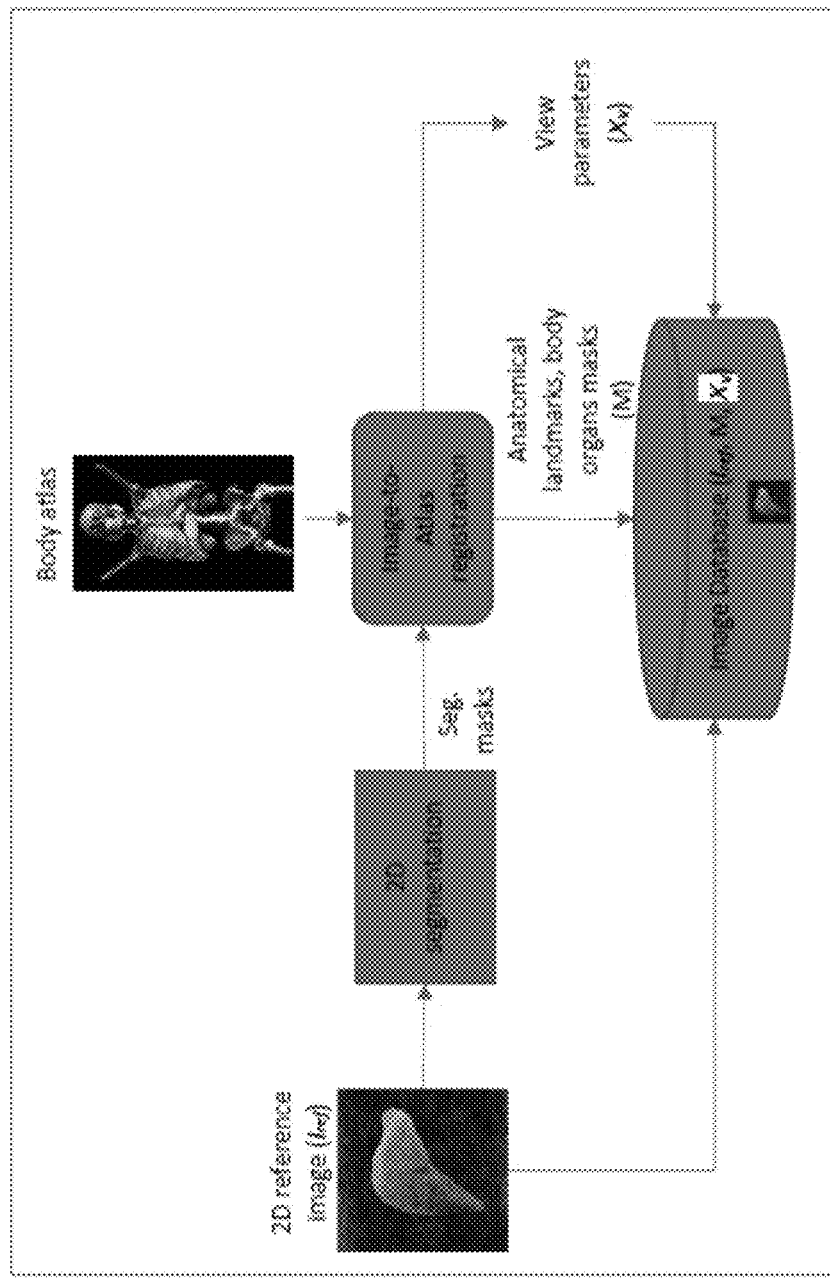
FIG. 3 depicts an example workflow for generating a template according to an embodiment.

At Act 210, a template database is generated from a plurality of reference images. The reference images may be or include a traditional anatomical illustration, a photograph of a surgical procedure, an MPR image, a previously rendered image, etc. Given the reference image (Iref), the system computes a 2D segmentation to generate a collection of anatomical landmarks and binary masks representing the body organs found in Iref. Next, a 2D/3D or 3D/3D registration is applied to the masks against a full body 3D anatomical atlas. The registration image-to-atlas could be achieved via a deep learning method. The viewing parameters (Xv) that would generate renderings that best approximate the reference image are computed from the registration matrix. The template database stores the tuples (Iref, M, Xv) consisting of the reference image, the generated masks, and the calculated viewing parameters. FIG. 3 depicts a workflow for generating clinically relevant templates. A 2D reference image is segmented and matched using an image to atlas registration. The reference images, segmented maps, and viewing parameters are stored in an image database. Generating templates may be performed at any point prior to applying the templates to new data.

At Act 220, the system 100 acquires new image data. The new image data may be medical imaging data acquired from a medical imaging device. The data, images, or imaging data is made available by or within the medical imaging device. Alternatively, the acquisition is from storage or memory, such as acquiring a previously created dataset from a picture archiving and communication system (PACS). A processor may extract the data from a picture archive communications system or a medical records database.

The image data is data representing a two-dimensional slice or a three-dimensional volume of the patient. For example, the image data represents an area or slice of the patient as pixel values. As another example, the image data represents a volume or three-dimensional distribution of voxels. The three-dimensional representation may be formatted as a stack or plurality of two-dimensional planes or slices. Values are provided for each of multiple locations distributed in two or three dimensions.

The data may be in any format. While the terms image and imaging are used, the image or imaging data may be in a format prior to actual display of the image. For example, the imaging data may be a plurality of scalar values representing different locations in a Cartesian or polar coordinate format different than a display format. As another example, the image may be a plurality red, green, blue (e.g., RGB) values output to a display for generating the image in the display format. The imaging data may be currently or previously displayed image in the display or another format. The imaging data is a dataset that may be used for imaging, such as scan data or a generated image representing the patient.

Any type of medical imaging data and corresponding medical scanner may be used to acquire the image data. In one embodiment, the imaging data is a computed tomography (CT) image acquired with a CT system. For example, a chest CT dataset may be acquired by scanning the lungs. The output image may be a two-dimensional image slice. For a three-dimensional CT image, the raw data from the detector is reconstructed into a three-dimensional representation. As another example, magnetic resonance (MR) data representing a patient is acquired with an MR system. The data is acquired using an imaging sequence for scanning a patient. K-space data representing an interior region of a patient is acquired. Fourier analysis is performed to reconstruct the data from the k-space into a three-dimensional object or image space. The data may be ultrasound data. Beamformers and a transducer array scan a patient acoustically. Received acoustic signals are beamformed and detected into polar coordinate ultrasound data representing the patient.

The imaging data represents tissue, fluid, and/or bone of the patient. For imaging the lungs, the imaging data may include response from the lungs and the anatomy around the lungs (e.g., upper torso). In other embodiments, the medical image represents both function (such as perfusion) as well as structure, such as nuclear medicine (NM) data.

At Act 230, the acquired image data is segmented into one or more segmentation masks. Any method for segmentation may be used. For example, segmentation may be thresholding-based, region-based, shape-based, model based, neighboring based, and/or machine learning-based among other segmentation techniques. Thresholding-based methods segment the image data by creating binary partitions based on image attenuation values, as determined by the relative attenuation of structures on the images. Region-based segmentation compares one pixel in an image to neighboring pixels, and if a predefined region criterion (e.g., homogeneity) is met, then the pixel is assigned to the same class as one or more of its neighbors. Shape-based techniques use either an atlas-based approach or a model-based approach to find a lung boundary. Model-based methods use prior shape information, similar to atlas-based approaches; however, to better accommodate the shape variabilities, the model-based approaches fit either statistical shape or appearance models of the lungs to the image by using an optimization procedure. Neighboring anatomy-guided methods use the spatial context of neighboring anatomic objects of the lung (e.g., rib cage, heart, spine) for delineating lung regions. In machine learning-based methods, the lung abnormalities and boundaries are predicted on the basis of the features extracted from the image data.

The output of act 230 is a collection of 3D binary masks (M) describing the segmentation of each anatomical region, each lesion and set of landmarks found. The masks may then be registered against a full body atlas in order to identify one or more relevant templates at act 240. In Act 240, one or more templates are identified in the template database that correspond to the one or more segmented masks and thus are relevant to the new image data. A database retrieval system may be used to find the most relevant templates from the template database. In an example, the identified templates share the same segmented organs and landmarks as the new image data. For example, a Covid-19 template might consist of one or two lung masks and several nodules; or a cervical spine surgical template would include masks corresponding to vertebrae c1-c7. In another example, when the reference image consists of an MPR image, a content-based image retrieval system (CBIR) can be used to find more precise templates. In this case not only the presence of the same masks is used to detect the best template but also the contents of the MPR and the scanned volume are compared.

At Act 250, a differentiable renderer computes one or more rendering parameters based on a style of the reference image. Once a template or set of templates are found, the viewing parameters $Xv$ found in the database are used to render an initial image from the new image data using some stored preset or random values for the "style parameters". Using a "style" differential renderer, the parameters ($Xm$, $Xt$, $Xl$) are estimated to minimize the difference between the rendered image and the reference image extracted from the database. A different approach, such as the use of deep learning methods may also be used to recover these parameters. For deep learning, a neural network may be used.

Figure 4:
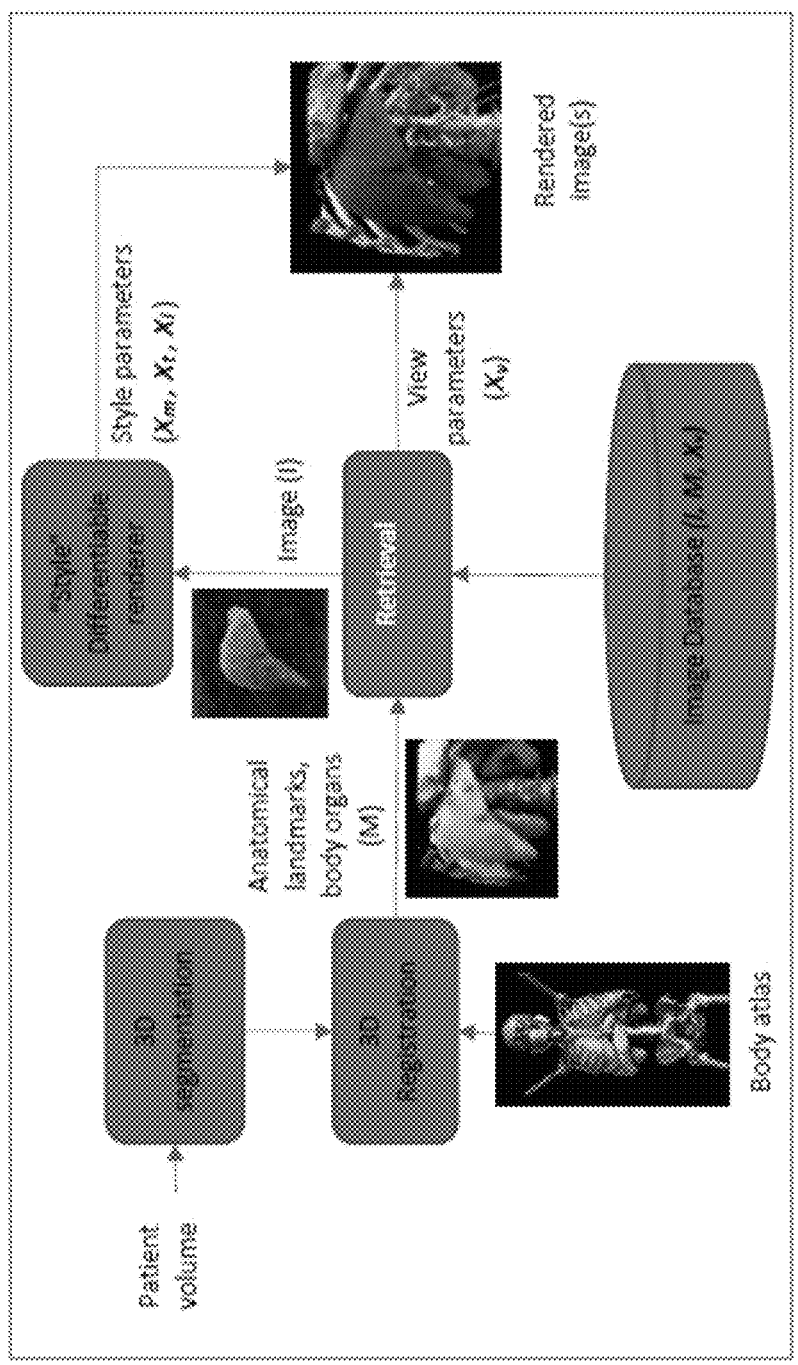
FIG. 4 depicts an example workflow for applying a template according to an embodiment.

At Act 260, the system 100 generates an image for the image data using the one or more rendering parameters and viewing parameters. FIG. 4 depicts an example workflow for applying the templates to new data sets. A patient volume is acquired, segmented, and registered with the body atlas. A template is received and used by a differentiable renderer to generate style parameters. The style parameters and view parameters are used to generate the rendered image.

Figure 5:
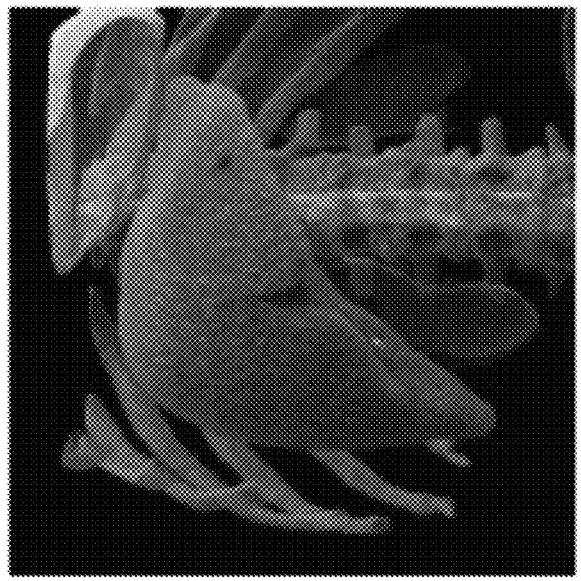
FIG. 5 depicts an example of the results of applying a template according to an embodiment.
Figure 5:
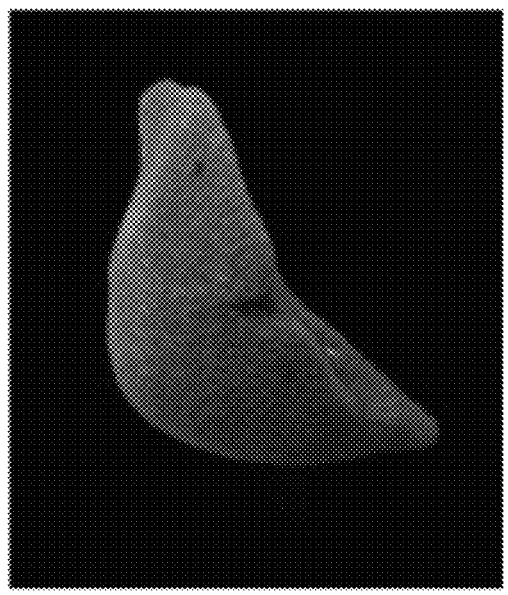

In another embodiment, a scan not fully compatible with a template may be rendered with the missing information coming from the anatomical atlas for additional context. For example, a template consisting of the liver, rib cage and spine may be applied to a volume of a segmented liver by adding to the final rendering the missing anatomical structures from the atlas. FIG. 5 depicts how a template consisting of the liver, rib cage and spine can be applied to a volume of a segmented liver by adding to the final rendering the missing anatomical structures from the atlas.

Figure 6:
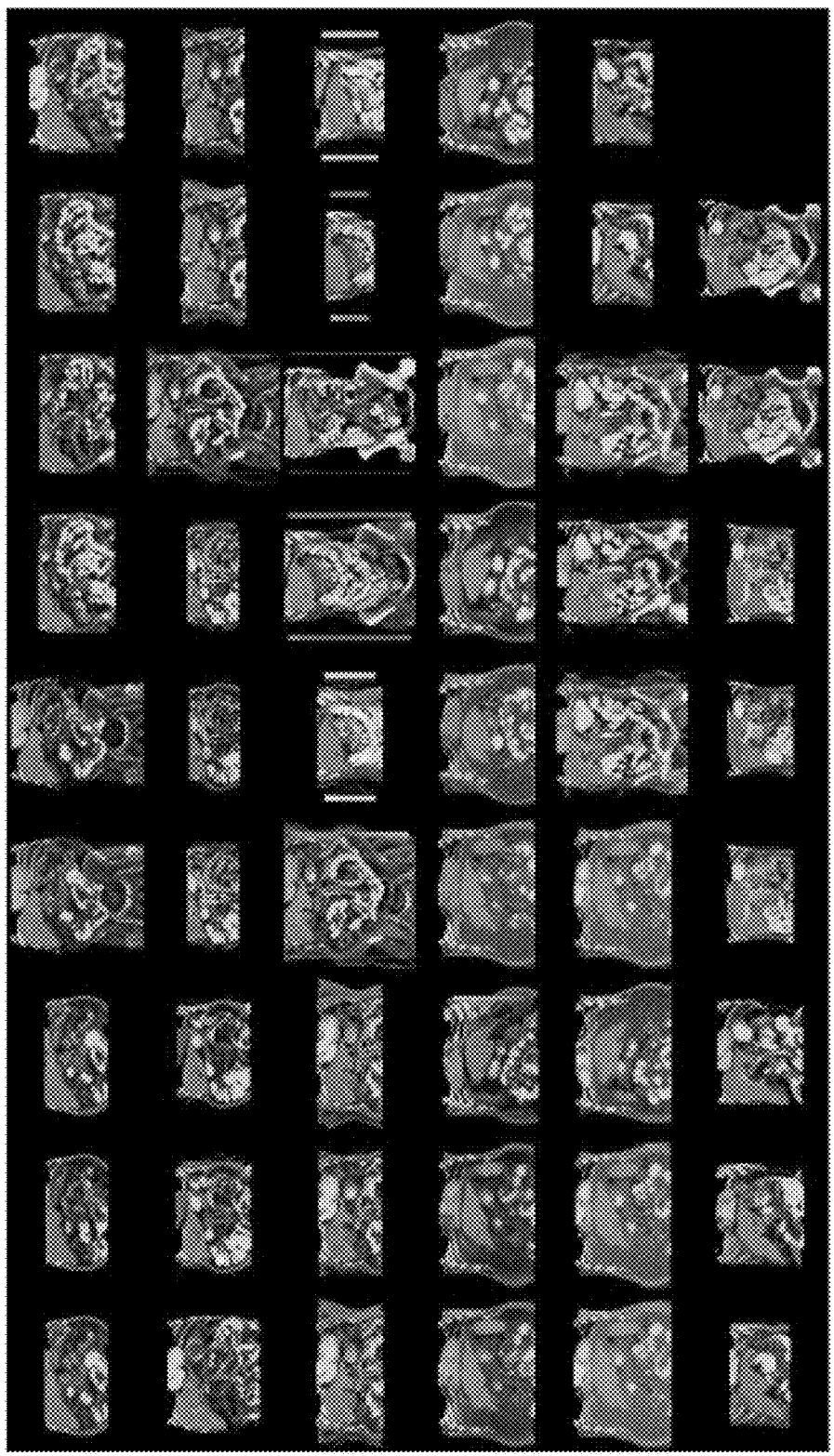
FIG. 6 depicts another example of the results of applying a template according to an embodiment.
Figure 7:
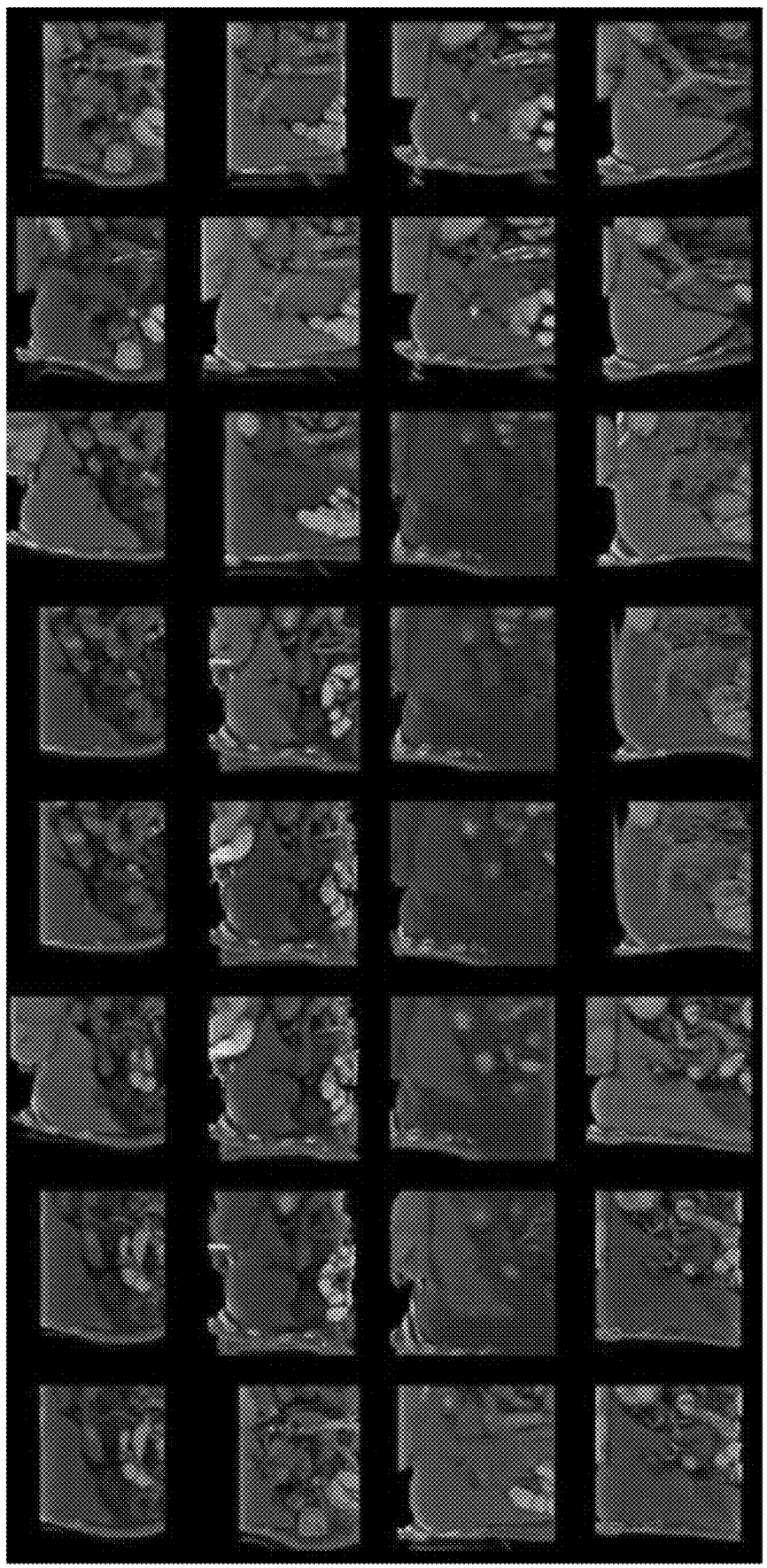
FIG. 7 depicts another example of the results of applying a template according to an embodiment.

FIG. 6 illustrates how a windowing template could be applied to abdominal scans with diverse acquisition protocols and still generate consistent renderings in terms of visual impression. FIG. 7 illustrates the result of applying a viewing template to datasets containing the liver to generate consistent position and orientations.

Figure 8:
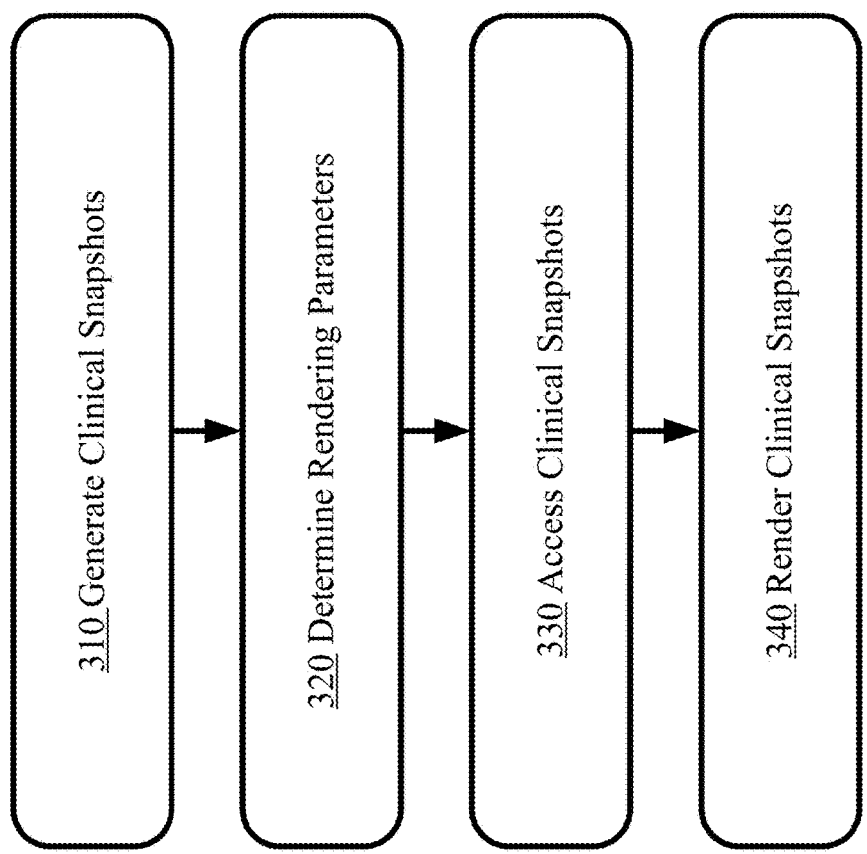
FIG. 8 depicts an example method for rendering medical imaging data for an interactive viewer according to an embodiment.

One method to generate a template is by using the authoring platform as described above. FIG. 8 depicts a method for photorealistic interactive viewing of 3D and 4D medical data based on authored clinical snapshots. The acts are performed by the system of FIG. 1, FIG. 12, other systems, a workstation, a computer, and/or a server. The acts are performed in the order shown (e.g., top to bottom) or other orders.

Embodiments address the challenges of viewing such data on platforms with real-time requirements, such as Augmented- and Virtual-Reality devices while maintaining the quality of the original authored content. When using devices or hardware that cannot run an advance rendering algorithm, a simplified algorithm is used for interactive approximate global illumination during volume rendering, as well as pre-rendered assets at various stages of the rendering pipeline. In certain embodiments, the method is implemented by a system containing one or more of the following components: an authoring platform (input interface 110), a viewing platform 130, and a navigation interface. The authoring platform is used to generate clinical content based on photorealistic rendering of medical volume data, with manual and automated snapshot authoring tools. The authoring platform may be part of the input interface 110 and may include some image processing capabilities of the image processing system 120.

The authoring platform provides for clinically relevant snapshots of the patient medical data to be created by experts to, for example, support educational or clinical workflows. Alternatively, snapshots are created by automation processes from AI-based organ and disease segmentations. In an embodiment, Snapshots store rendering parameter sets for viewing, clipping, classification, animations and rendering styles. The viewing interface is configured to provide a view of the image data to an end user. In an embodiment, the viewing interface is an AR or VR system that provides interactive real time viewing to a user. The Viewing interface is configured to provide real-time rendering of the authored clinical content based on approximate global illumination and pre-computed data. The navigation application is configured to provide 3D user interfaces, for example, based on pre-computed holograms from the clinical snapshots.

The system optimizes the rendering parameters for different rendering algorithms, for example, the interactive approximate global illumination method and the volume rendering proxy generation based on authored clinical snapshots. The pre-computed rendering techniques and parameters provide realistic graphics closer to the quality of the authored content at low performance cost during interactive exploration.

At Act 310, an authoring platform generates one or more clinical snapshots for a medical imaging scenario using a first rendering algorithm. The clinical snapshot specifies one or more visualization settings for the medical imaging scenario. The visualization settings may include rendering parameters provided at act 320. Pre-computed assets may also be used to define or supplement the one or more visualization settings.

At Act 320, the authoring platform optimizes rendering parameters for one or more alternative rendering algorithms. The optimized rendering parameters approximate the one or more visualization settings from the one or more clinical snapshots. The authoring platform pre-computes the rendering parameters so that interactive rendering using the second rendering algorithm (which may be quicker and use fewer resources) better approximates the full-quality authored assets. For example, the authoring platform is used to generate a high-quality clinical snapshot. The authoring platform then pre-computes placement, intensity and color of synthetic light sources for the interactive renderer to approximate the image-based lighting volumetric path tracer in the authoring platform. The style/visualization settings of the authored clinical snapshot are thus transferred/maintained when viewing and navigating the snapshot using a machine or device that may not be able to provide cinematic rendering.

Traditional volume visualization methods based on ray casting, which are still used in many visualization medical products, simulate only the emission and absorption of radiant energy along the primary viewing rays through the volume data. The emitted radiant energy at each point is absorbed according to the Beer-Lambert law along the ray to the observer location with absorption coefficients derived from the patient data. Renderers typically compute shading using only the standard local shading models at each point along the ray (e.g., the Blinn-Phong model), based on the local volume gradients (local illumination). While fast, these methods do not simulate the complex light scattering and extinction associated with photorealism (global illumination). In contrast, the authoring platform may implement a physically based Monte Carlo light transport, which simulates light paths though the volume data with multiple scattering events per path using a stochastic process. As more and more paths are simulated, the solution converges on an accurate estimation of the irradiance at each point for incoming light from all directions. The renderer for the authoring platform employs a hybrid of volumetric scattering and surface-like scattering, modeled by phase functions and BRDFs respectively, based on properties derived from the anatomical data.

Accordingly, when created and manipulated by the authoring platform, the medical data is illuminated using image-based lighting by high dynamic range light probes, that may be acquired photographically with 360-degree cameras in order to resemble the lighting condition of the training theater. Such lighting leads to a more natural appearance of the data when compared to images created using the synthetic light sources that are typically applied in direct volume rendering methods. When also combined with the accurate simulation of photon scattering and absorption, the authoring platform is able to produce/author photorealistic images that contain many shading effects observed in nature, such as soft shadows, ambient occlusions, volumetric scattering, and subsurface photon interactions. The result is a hyper-realistic augmented experience that appears natural and intuitive without the technology being a distraction to achieving efficient learning.

However, when sampling, the convergence of the light transport simulation is accelerated considerably, up to the performance required for interactive, but not for real-time applications. For AR deployments with real-time and low latency requirements, the authoring platform may further pre-compute, cache, and re-use parts of the light transport simulations with certain simplifying assumptions that have limited impact on the final image quality. Specifically, the authoring platform may compute forward chromatic scattering of light only with local-only shading based on synthetic light environment approximating the light probe. The results of the light propagation are saved to a separate lighting volume, recomputed on lighting changes and used as the shadowing and global illumination terms in a high-performance ray casting algorithm, which renders soft shadows and subsurface light scattering at real-time speeds.

To enable real-time rendering for the scenarios described here, the system employs pre-computed rendering techniques that enable realistic graphics closer to the quality of the authored content at low performance cost during interactive exploration. The authoring platform may also pre-compute static lighting volumes to correct for the difference between the interactive and off-line rendering (applicable to mesh proxies as well). The authoring platform may also account for expected parameter replacements by the viewing platform—e.g., optimize lighting parameters for the viewing parameters expected for head-tracked VR and AR displays. In addition, the authoring platform may optimize shading, transparency and point placement when generating the point-cloud proxies. E.g., increase point cloud density in areas of the volume data with high frequency lighting or many overlapping surfaces (applicable to ray selection for light field generation too). In an embodiment, the optimization process may employ differentiable rendering as described above to determine the rendering parameters.

Figure 9:
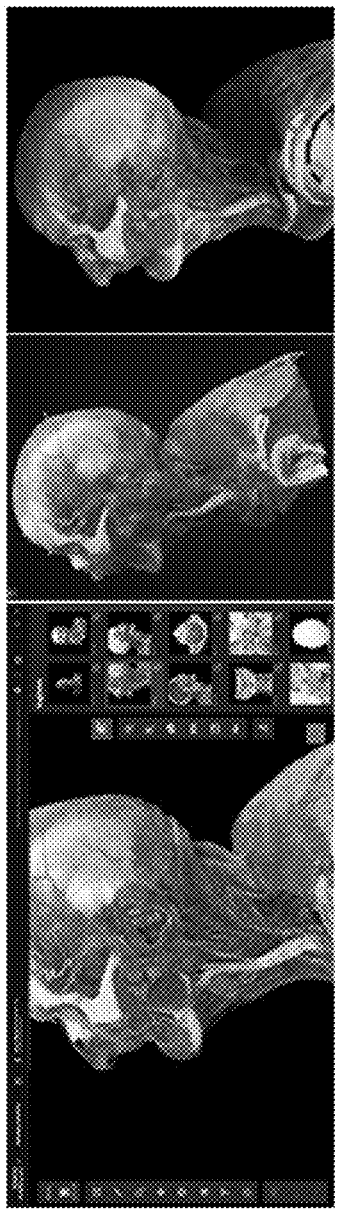
FIG. 9 depicts an example of the results of rendering a clinical snapshot according to an embodiment.
Figure 9:

At Act 330, a viewing platform 130 accesses the one or more clinical snapshots. The viewing platform 130 uses, for example, the second rendering algorithm. At Act 340, the viewing interfaces renders, using the second rendering algorithm using the rendering parameters, image data for interactive viewing of the one or more clinical snapshots. The viewing platform 130 may employ the same or different rendering algorithms than the authoring platform. In one embodiment, an interactive version of the Monte Carlo volumetric path tracing may be used together with temporal reprojection, upsampling and denoising when the viewing platform contain high-end GPUs. Alternatively, fast volume raycasting may be used for interactive viewing, optionally with approximate global illumination and/or leveraging pre-computed illumination from the authoring platform. FIG. 9 depicts one example of the results of the method, where the authored clinical snapshots are approximated by point clouds or a single surface mesh with baked global illumination. FIG. 9 further depicts frames from a pre-rendered turntable animation, which is suitable for use on viewing platforms without 3D rendering capabilities while still allowing a minimal amount of interaction by seeking through the decoded video.

Figure 10:
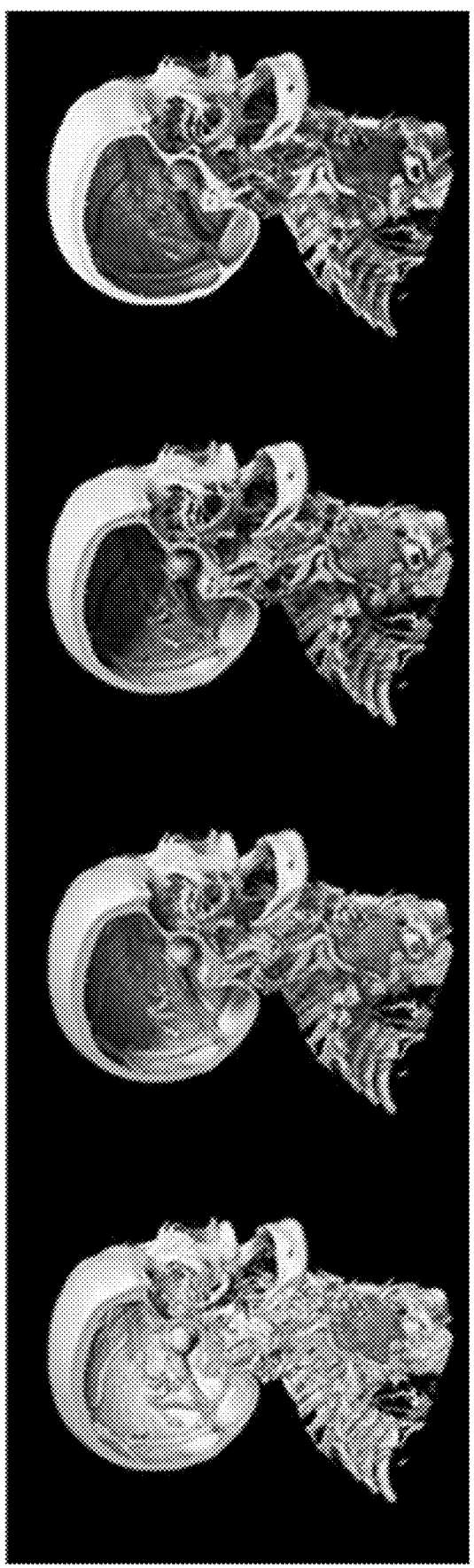
FIG. 10 depicts another example of the results of rendering a clinical snapshot according to an embodiment.

FIG. 10 illustrates rendering options in one embodiment of the system. FIG. 10 includes four views including a) Local shading only; b) approximate global illumination with synthetic light source; c) offline volumetric path tracing with synthetic light source; and d) offline volumetric path tracing with image-based lighting. The interactive approximate lighting (b) approximates the offline full quality solution reasonably well (c), even though some of the complex light interactions with matter are missing. (d) shows volumetric path tracing with image-based lighting (HDR lightprobes), which can be approximated during interactive rendering using irradiance caching approaches.

Figure 11:
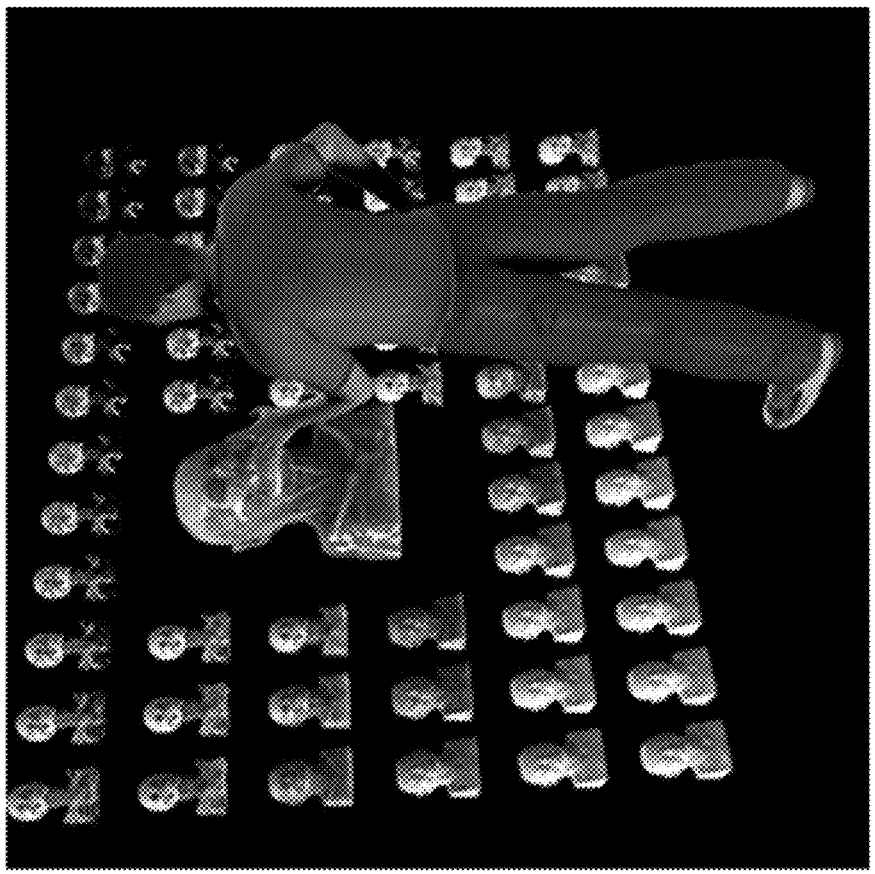
FIG. 11 depicts another example of the results of rendering a clinical snapshot and an interactive viewer according to an embodiment.

FIG. 11 depicts the use of clinical snapshots in an interactive VR viewing platform where the viewing specification of the snapshots is replaced by the headtracking data. The lighting is replaced with an exterior directional light source aligned to the user's hand. The lighting parameters are set to approximate the soft lighting preset from the authoring application.

In some embodiments, the viewing platform 130 implements an exploratory interface for the authored snapshots based on the concept of Surround Galleries. The various pre-computed representations or real time rendering are used depending on the capabilities and requirements of the display hardware (e.g., use pre-computed videos instead of 3D spatial holograms for non-stereoscopic, non-immersive displays). Transitions between snapshots are animated with support from the authoring system in order to reduce the mental load of the user by preserving the anatomical context while structures from the selected snapshots are faded in. Additional embodiments allow for visual comparison by manipulating the holograms of multiple snapshots in various spatial layouts like in FIG. 11.

For viewing platforms 130 with sufficient computational resources, live editing of parameter sets covered or not covered by the pre-computed assets and resources may be enabled, e.g., moving the clipping plane of the authored preset. For example, for a fully precomputed lightfields, if the user changes the clipping, which is not covered by the pre-computed lightfield, the viewing platform may switch to a lower quality real-time rendering algorithm. In such cases, a visual indicator may show that the system 100 is in an interactive editing state and allow the user to revert to using the pre-computed higher quality assets.

In room-scale immersive environments tracking of users may also be used to drive the visualizations. E.g., multiple pre-computed visualizations can be rendered on a large display, and as individual users approach holograms, the visualizations may be enlarged, and more information about the corresponding visualization can be shown. Multiple users can be tracked in a shared virtual environment, and relevant information can be shown to each user based on the individual view. In an embodiment, various parts of the visualization can be authored by multiple users. A dataset could be segmented using automated algorithms, annotated by a radiologist, and tweaked for rendering by a visualization expert. The users can then be served annotations and segmentation masks based on their view, expertise, or clinical role. In an embodiment, multiple users could be using separate mobile devices like iPads in a shared physical space for a shared viewing experience. In an embodiment, such users may be allowed to change the rendering parameters for their individual visualizations. In another embodiment, the rendering settings may be shared such that when some of the settings are changed by a user, the visualization changes for all other users as well.

Figure 12:
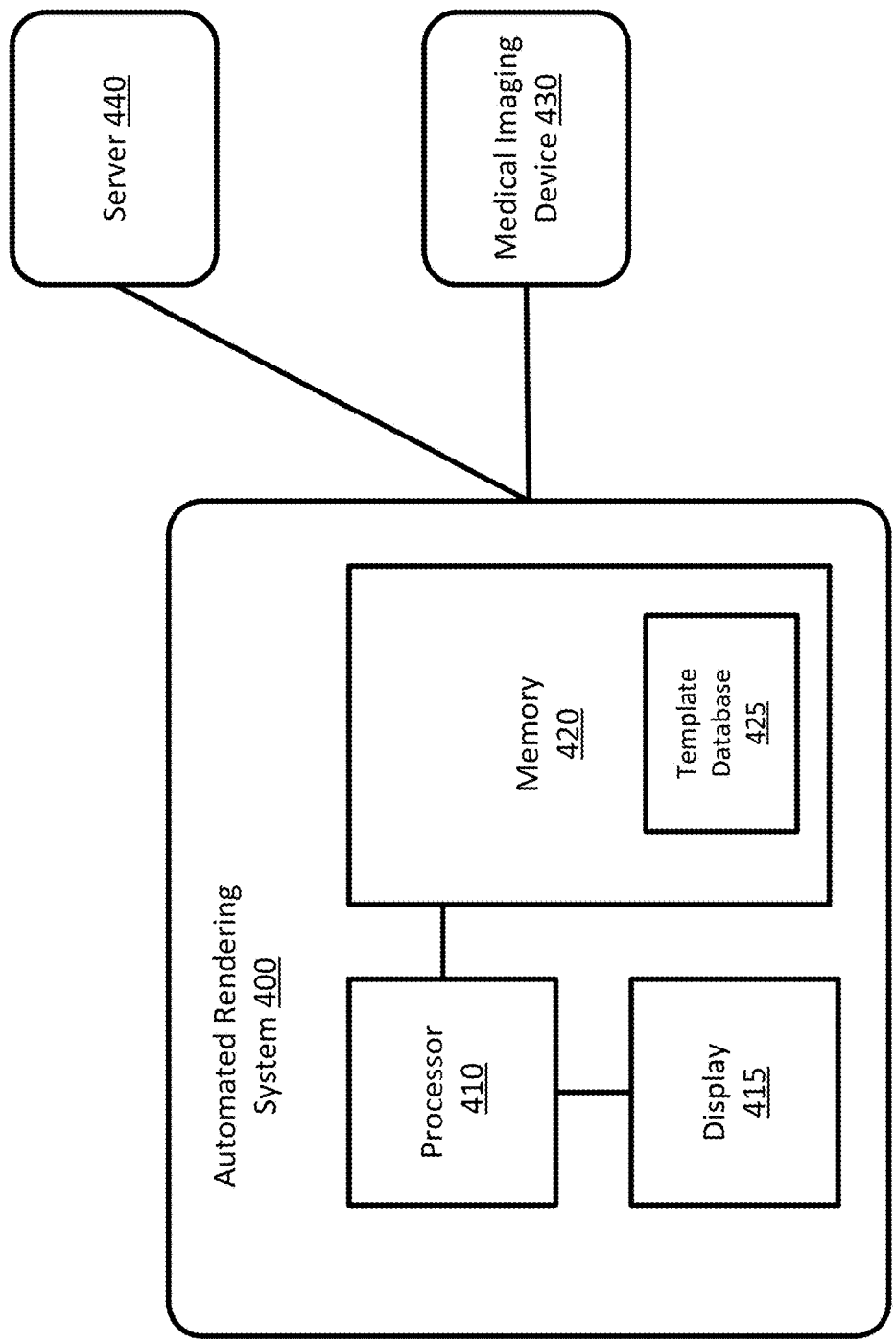
FIG. 12 depicts an example of an automated rendering system according to an embodiment.

FIG. 12 shows one embodiment of an automated rendering system 400/image processing system 110. The automated rendering system 400 includes a display 415, memory 420, and image processor 410. The display 415, image processor 410, and memory 420 may be part of a medical imaging device 430 (e.g., CT scanner), a computer, server 440, workstation, or other system for image processing medical images from a scan of a patient. A workstation or computer without the medical scanner 430 may be used as the automated rendering system 400. Additional, different, or fewer components may be provided. For example, a computer network is included for remote image generation of locally acquired image data by the server 440. As another example, a user input device (e.g., keyboard, buttons, sliders, dials, trackball, mouse, or other device) is provided. In another example, an interactive viewing platform for AR or VR is provided. In yet another example, the medical scanner 430 is not provided.

The image data, templates, authored snapshots, rendering parameters, display image, and/or other information are stored in a non-transitory computer readable memory, such as the memory 420. In an example, a template database 425 is stored in the memory 420. The template database 425 may include at least reference images, view parameters, masks, etc. The memory 420 is or includes an external storage device, RAM, ROM, database, and/or a local memory (e.g., solid state drive or hard drive). The same or different non-transitory computer readable media may be used for the instructions and other data. The memory 420 may be implemented using a database management system (DBMS) and residing on a memory, such as a hard disk, RAM, or removable media. Alternatively, the memory 420 is internal to the processor 410 (e.g., cache). The instructions for implementing the authoring, generating, rendering, or application processes, the methods, and/or the techniques discussed herein are provided on non-transitory computer-readable storage media or memories, such as a cache, buffer, RAM, removable media, hard drive, or other computer readable storage media (e.g., the memory 420). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The image processor 410 is a controller, control processor, general processor, micro-processor, tensor processor, digital signal processor, three-dimensional data processor, graphics processing unit, application specific integrated circuit, field programmable gate array, artificial intelligence processor, digital circuit, analog circuit, combinations thereof, or other now known or later developed device for processing image data. The image processor 410 is a single device, a plurality of devices, or a network of devices. For more than one device, parallel or sequential division of processing may be used. Different devices making up the image processor 410 may perform different functions. In one embodiment, the image processor 410 is a control processor or other processor of the medical scanner 430. The image processor 410 operates pursuant to and is configured by stored instructions, hardware, and/or firmware to perform various acts described herein.

The image processor 410 is configured to generate rendering of new data that are similar to rendering for templates that are already in a database stored in the memory 420. The image processor 401 is further configured to create a database of templates, wherein each template includes a reference image, masks, and viewing parameters. The image processor 410 is configured to use the templates to render new data. The image processor 410 is configured to segment new data, find all the landmarks etc., register the segmented new data against a full body atlas to identify the content or features of the new data. The identified content/features are used to retrieve a template from the database that resembles the volume due to content (location/disease/lesion). The image processor 410 uses a differentiable renderer or other technique to apply the style of the template to the new data.

The image processor 410 is configured to pre-compute rendering parameters for different rendering algorithms based on an authored clinical snapshot. The image processor 410 attempts to generate rendering parameters used by the renderer to produce images that look as close as possible to the authored content even though a viewing platform may be using different rendering techniques.

The image processor 410 may be configured to implement one or more machine trained networks. The network(s) may be defined as a plurality of sequential feature units or layers. The general flow of output feature values may be from one layer to input to a next layer. The information from the next layer is fed to a next layer, and so on until the final output. The layers may only feed forward or may be bi-directional, including some feedback to a previous layer. Skip connections may be provided where some information from a layer is feed to a layer beyond the next layer. The nodes of each layer or unit may connect with all or only a sub-set of nodes of a previous and/or subsequent layer or unit. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. Other network arrangements may be used, such as a support vector machine. Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (e.g., including different weights for different areas of the states). The training of CNN is entirely discriminative through back-propagation. DBN, on the other hand, employs the layer-wise unsupervised training (e.g., pre-training) followed by the discriminative refinement with back-propagation if necessary. In an embodiment, the arrangement of the machine learnt network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

For training, the network inputs training data and generates an output. The output is compared to the training data. A loss function may be used to identify the errors from the comparison. The loss function serves as a measurement of how far the current set of predictions are from the corresponding true values. Some examples of loss functions that may be used include Mean-Squared-Error, Root-Mean-Squared-Error, and Cross-entropy loss. Mean Squared Error loss, or MSE for short, is calculated as the average of the squared differences between the predicted and actual values. Root-Mean Squared Error is similarly calculated as the average of the root squared differences between the predicted and actual values. During training and over repeated iterations, the network attempts to minimize the loss function as the result of a lower error between the actual and the predicted values means the network has done a good job in learning. Different optimization algorithms may be used to minimize the loss function, such as, for example, gradient descent, Stochastic gradient descent, Batch gradient descent, Mini-Batch gradient descent, among others. The process of inputting, outputting, comparing, and adjusting is repeated for a predetermined number of iterations with the goal of minimizing the loss function.

The display 415 is a CRT, LCD, projector, plasma, printer, tablet, smart phone, head mounted display (HMD) or other now known or later developed display device for displaying the output (e.g., image from the medical imaging device 430). The display 415 may also be part of the viewing platform 130. The display may include other types of displays such as auto-stereo display, light field displays (LFD), projected displays, etc. LFDs are based on a dense "field" of light rays produced by either a high-resolution LCD panel (with optics) or a projector array system. The result is a naturally viewable full-color real-time video 3D display that does not require any glasses. Projection mapping or projected augmented reality may be used, if for example, a camera/projector is used instead of a head mounted display. For projection AR, the projector projects a beam of light onto the work surface or, for example, directly on the parts on which the user is interacting with. 3D displays or stereo displays present normal two-dimensional (2D) images offset laterally by a small amount and displayed separately to the left and right eye. Both of these 2D offset images are then combined in the brain and create the perception of depth.

The medical imaging device 430 is a diagnostic scanner. The medical imaging device 430 operates pursuant to one or more settings to scan a patient resting on a bed or table. The settings control scanning including transmission, reception, reconstruction, and image processing. A scanning protocol is followed to generate data representing the patient, such as CT image data representing part of the patient. The patient is imaged by the scanner using the settings.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

The invention claimed is:

1. A method for automated rendering from templates, the method comprising:
    acquiring, by a medical imaging device, medical image data of a patient;
    segmenting the medical image data into one or more segmentation masks;
    retrieving one or more templates corresponding to the one or more segmentation masks, the one or more templates comprising at least a reference image and viewing parameters;
    computing, using a differentiable renderer, one or more rendering parameters based on a style of the reference image, the rendering parameters comprising at least lighting parameters, material properties, and transfer functions; and
    generating an image for the medical image data using the one or more rendering parameters.

2. The method of claim 1, wherein retrieving the one or more templates comprises registering the one or more segmentation masks against a body atlas configured to store a plurality of different masks of different regions and organs.

3. The method of claim 1, wherein the one or more templates are generated from a traditional anatomical illustration or a photograph.

4. The method of claim 1, wherein the one or more rendering parameters define a color and a texture of the generated image.

5. The method of claim 1, wherein the one or more templates comprise at least reference images for different organs.

* * * * *